United States Patent
Kirk et al.

(10) Patent No.: US 8,148,900 B1
(45) Date of Patent: Apr. 3, 2012

(54) METHODS AND SYSTEMS FOR PROVIDING ILLUMINATION OF A SPECIMEN FOR INSPECTION

(75) Inventors: Greg Kirk, Pleasanton, CA (US); Rich Solarz, Danville, CA (US)

(73) Assignee: KLA-Tencor Technologies Corp., Milpitas, CA (US)

(*) Notice: Subject to any disclaimer, the term of this patent is extended or adjusted under 35 U.S.C. 154(b) by 1109 days.

(21) Appl. No.: 11/623,981

(22) Filed: Jan. 17, 2007

Related U.S. Application Data

(60) Provisional application No. 60/759,846, filed on Jan. 17, 2006, provisional application No. 60/772,425, filed on Feb. 9, 2006.

(51) Int. Cl.
*H01J 65/00* (2006.01)

(52) U.S. Cl. ......... 313/607; 362/263; 315/248; 356/369

(58) Field of Classification Search ............ 313/153, 313/172, 318.01; 315/248; 362/263
See application file for complete search history.

(56) References Cited

U.S. PATENT DOCUMENTS

| | | | |
|---|---|---|---|
| 5,686,793 A * | 11/1997 | Turner et al. | 313/570 |
| 5,798,618 A * | 8/1998 | van Os et al. | 315/248 |
| 5,864,394 A | 1/1999 | Jordan, III et al. | |
| 6,157,141 A * | 12/2000 | Lapatovich et al. | 315/248 |
| 6,265,813 B1 * | 7/2001 | Knox et al. | 313/113 |
| 6,313,467 B1 | 11/2001 | Shafer et al. | |
| 6,507,031 B1 | 1/2003 | Jinbo et al. | |
| 6,633,831 B2 | 10/2003 | Nikoonahad et al. | |
| 6,655,810 B2 * | 12/2003 | Hayashi et al. | 362/600 |
| 6,862,096 B2 | 3/2005 | Vaez-Iravani et al. | |
| 6,879,391 B1 | 4/2005 | Danko | |
| 2004/0036393 A1 * | 2/2004 | Eastlund et al. | 313/26 |
| 2004/0201837 A1 | 10/2004 | Lange et al. | |
| 2005/0052643 A1 | 3/2005 | Lange et al. | |
| 2005/0252752 A1 | 11/2005 | Fielden et al. | |
| 2005/0254050 A1 * | 11/2005 | Fielden et al. | 356/369 |
| 2008/0258085 A1 * | 10/2008 | Bauer | 250/504 R |

OTHER PUBLICATIONS

U.S. Appl. No. 11/771,430, filed Jun. 29, 2007, Kirk et al.
Babucke et al., "On the energy balance in the core of electrode-stabilized high-pressure mercury discharges," J. Phys. D: Appl. Phys. 24. (1991) pp. 1316-1321.
Derra et al., "UHP lamp systems for projectino applications," J. Phys. D: Appl. Phys. 38 (2005) pp. 2995-3010.
Wilbers et al., "The VUV Emissivity of a high-pressure cascade argon arc from 125 to 200 nm," J. Quant. Spectrosc. Radiat. Transfer, vol. 46, No. 4, 1991, pp. 299-308.

(Continued)

*Primary Examiner* — Toan Ton
*Assistant Examiner* — Andrew Coughlin
(74) *Attorney, Agent, or Firm* — Ann Marie Mewherter

(57) ABSTRACT

Methods and systems for providing illumination of a specimen for inspection are provided. One embodiment relates to a system configured to provide illumination of a specimen for inspection. The system includes an electrodeless lamp configured to generate light. The system is further configured such that the light illuminates the specimen during the inspection. Another embodiment relates to a system configured to inspect a specimen. The system includes an electrodeless lamp configured to generate light and one or more optical elements configured to direct the light to the specimen. The system also includes a detection subsystem configured to generate output responsive to light from the specimen. The output can be used to detect defects on the specimen. An additional embodiment relates to a method for providing illumination of a specimen for inspection. The method includes illuminating the specimen during the inspection with light generated by an electrodeless lamp.

37 Claims, 2 Drawing Sheets

OTHER PUBLICATIONS

Erskine et al., "Measuring Opacity of Shock Generated Argon Plasmas," J. Quant. Spectrosc. Radiat. Transfer, vol. 51, No. 51, No. 1/2, 1994, pp. 97-100.

Smith, David, "Gas-Breakdown Dependence on Beam Size and Pulse Duration with 10.6-u Wavelength Radiation," Journal of Applied Physics, vol. 19, No. 10, Nov. 15, 1971, pp. 405-408.

Jeng et al., "Theoretical investigation of laser-sustained argon plasmas," J. Appl. Phys. vol. 60, No. 7, Oct. 1, 1986, pp. 2272-2279.

Kozlov et al., "Radiative losses by argon plasma and the emissive model of a continuous optical discharge," Sov. Phys-JETP, vol. 39, No. 3, Sep. 1974, pp. 463-468.

Cohn et al., "Magetic-Field-Dependent Breakdown of CO2-Laser-Produced Plasma," Appl. Phys. Lett., vol. 20, No. 6, Mar. 15, 1972, pp. 225-227.

Franzen, "cw gas breakdown in argon using 10.6-um laser radiation," Appl. Phys. Lett., vol. 21, No. 2, Jul. 15, 1972, pp. 62-64.

Harilal et al., "Influence of ambient gas on the temperature and density of laser produced carbon plasma," Appl. Phys. Lett. 72 (2) Jan. 1, 1998, pp. 167-169.

D. L. Franzen, "Continuous laser-sustained plasmas," J. Appl. Phys. 44(4), pp. 1727-1732 (1972).

R. Wiehle et al. "Dynamics of strong-field above-threshold ionization of argon: Comparison between experiment and theory," The American Physical Society, 2003, pp. 063405-1-063405-7.

V. V. Kostin et al., "Emission from a Plasma Heated by Short Laser Pulses," Plasma Physics Reports, vol. 23, No. 2, 1997, pp. 102-109.

A. Takahashi et al., "Ar2 excimer emission from a laser-heated plasma in a high-pressure argon gas," App. Phys. Lett., vol. 77, No. 25, Dec. 2000, pp. 4115-4117.

H. Tanaka et al., "Production of laser-heated plasma in high-pressure Ar gas and emission characteristics of vacuum ultraviolet radiation from Ar2 excimers," ppl. Phys. B, 74, 2002, pp. 323-326.

A. Takahashi et al., Numerical Analysis of Ar2 Excimer Production in Laser-Produced Plasmas, Jap. Journ. Appl. Phys., vol. 37, 1998, pp. L390-L393.

S. Schohl et al., "Absolute detection of metastable rare gas atoms by a cw laser photoionization method," Z. Phys. D—Atoms, Molecules and Clusters, 21(1), 1991, pp. 25-39.

Z. Szymanski et al., "Nonstationary laser-sustained plasma," J. Appl. Phys., 69(6), Mar. 1991, pp. 3480-3484.

Z. Szymanski et al., "Spectroscopic study of a supersonic jet of laser-heated argon plasma," J. Phys. D: App. Phys. 30, 1997, pp. 998-1006.

J. M. Girard et al. "Generating conditions of a laser-sustained argon plasma jet," J. Phys. D: App. Phys. 26, 1993, pp. 1382-1393.

A. B. Lewis et al., "Measurements of CW Photoionization for the use in stable high pressure tea laser discharge," 2nd Inter. Conf. on Plasma Science IEEE, May 1975, p. 45.

J. E. Daily et al., "Two-photonionization of the Ca 4s3d D2 level in an optical dipole trap," Phys. Rev. A, 71, 2005, pp. 043406-1-043406-5.

J. L. Emmett et al., "Direct Measurement of Xenon Flashtube Opacity," J. Appl. Phys., vol. 35, No. 9, Sep. 1964, pp. 2601-2604.

V. Malka et al., "Channel Formation in Long Laser Pulse Interaction with a Helium Gas Jet" Phys. Rev. Lett., vol. 79, No. 16, Oct. 1997, pp. 2979-2982.

K. Krushelnick et al. "Plasma Channel Formation and Guiding during High Intensity Short Pulse Laser Plasma Experiments," Phys. Rev. Lett., vol. 78, No. 21, May 1997, pp. 4047-4050.

S. P. Nikitin et al. "Guiding of intense femtosecond pulses in preformed plasma channels," Optics Letters, vol. 22, No. 23, Dec. 1997, pp. 1787-1789.

* cited by examiner

ME THODS AND SYSTEMS FOR PROVIDING
ILLUMINATION OF A SPECIMEN FOR
INSPECTION

PRIORITY CLAIM

This application claims priority to U.S. Provisional Application Nos. 60/759,846 entitled "Methods and Systems for Providing Illumination of a Specimen for Inspection," filed Jan. 17, 2006 and 60/772,425 entitled "Methods and Systems for Providing Illumination of a Specimen for Inspection," filed Feb. 9, 2006, which are incorporated by reference as if fully set forth herein.

BACKGROUND OF THE INVENTION

1. Field of the Invention

The present invention generally relates to methods and systems for providing illumination of a specimen for inspection. Certain embodiments relate to methods and systems for providing illumination of a specimen for inspection using an electrodeless lamp.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. When inspecting specular or quasi-specular surfaces such as semiconductor wafers, bright field (BF) and dark field (DF) modalities are used. In BF inspection systems, collection optics are positioned such that the collection optics capture a substantial portion of the light specularly reflected by the surface under inspection. In contrast, in DF inspection systems, the collection optics are positioned out of the path of the specularly reflected light such that the collection optics capture light scattered by objects on the surface being inspected such as microcircuit patterns or contaminants on the surfaces of wafers.

Many different light sources have been used in inspection systems. For example, electrode based, relatively high intensity discharge arc lamps are used in inspection systems. However, these light sources have a number of disadvantages. For instance, electrode based, relatively high intensity discharge arc lamps have brightness limits and power limits due to electrostatic constraints on current density from the electrodes, the limited emissivity of gases as black body emitters, the relatively rapid erosion of electrodes made from refractory materials due to the presence of relatively large current densities at the cathodes, and the inability to control dopants (which can lower the operating temperature of the refractory cathodes) for relatively long periods of time at the required emission current.

Light emitting plasmas that are pumped by infrared lasers have been developed for various applications. For instance, some carbon dioxide laser produced plasmas have been produced and studied though not disclosed for use as imaging light sources or in wafer or reticle inspection applications. Examples of such plasmas are described in: Smith, Appl. Phys. Lett., 19(10), 405-408 (1971), S. Jeng and D. Keefer, Journal of Applied Physics, (7), 2272-2279, (1986), G. I. Kozlov, V. A. Kuznetsov, and V. A. Masyukov, Soviet Physics JETP, (39), 463-, (1974), which are incorporated by reference as if fully set forth herein.

Accordingly, it may be advantageous to develop electrodeless light sources for inspection applications, for example, by optimizing the operation of deep ultraviolet (DUV) electrodeless lamps for use as sources in applications for inspection such as semiconductor wafer inspection, and such optimization may include optimizing the pressure, gas type, energy deposition, and energy deposition profile of the lamp while at the same time eliminating the need for electrodes.

SUMMARY OF THE INVENTION

The following description of various embodiments of methods and systems is not to be construed in any way as limiting the subject matter of the appended claims.

One embodiment relates to a system configured to provide illumination of a specimen for inspection. The system includes an electrodeless lamp configured to generate light. The system is further configured such that the light illuminates the specimen during the inspection.

In one embodiment, the electrodeless lamp has an emissivity of greater than about 0.1. In another embodiment, the light generated by the electrodeless lamp includes deep ultraviolet light, ultraviolet light, visible light, or some combination thereof. In an additional embodiment, the light generated by the electrodeless lamp includes broadband light. In some embodiments, the light generated by the electrodeless lamp includes light in a band from about 180 nm to about 450 nm. In a further embodiment, the light generated by the electrodeless lamp includes light in a spectral region from about 200 nm to about 450 nm. In yet another embodiment, the electrodeless lamp includes a plasma from which collected radiation between about 200 nm and about 450 nm is greater than about 3 W.

In one embodiment, the electrodeless lamp has a partial pressure in a range of about 1 atm to about 40 atm. In another embodiment, a fill pressure of gases in the electrodeless lamp is about 4 atm or higher. In an additional embodiment, the electrodeless lamp includes a plasma at a temperature of about 10,000 K to about 30,000 K. In a further embodiment, the electrodeless lamp includes a plasma at a temperature of about 9,000 K to about 20,000 K. In yet another embodiment, the electrodeless lamp is at a pressure of above about 1 atm at a working temperature of the electrodeless lamp. In one such embodiment, the light generated by the electrodeless lamp includes light in a spectral region from about 200 nm to about 400 nm.

In one embodiment, the light generated by the electrodeless lamp has a spectral brightness exceeding about 2 W/mm$^2$-sr in an integral region of an electromagnetic spectrum from about 200 nm to about 400 nm. In another embodiment, the light generated by the electrodeless lamp has an average power in excess of about 3 W within any band in a region between about 200 nm and about 450 nm.

In one embodiment, the electrodeless lamp includes a plasma having a plasma axis length, and the plasma does not produce an average plasma opacity over the plasma axis length of greater than about 1 e-folding from one end cap to another end cap of the electrodeless lamp. In another embodiment, a fill gas in the electrodeless lamp has an opacity at a working temperature and pressure of the electrodeless lamp that does not exceed about 10% reabsorption of about 200 nm to about 450 nm radiation emitted from a center of the electrodeless lamp.

In one embodiment, the electrodeless lamp includes a plasma generated using a single gas. In another embodiment, the electrodeless lamp includes a plasma generated using a combination of gases. In an additional embodiment, the electrodeless lamp is filled with a gas that includes argon, krypton, xenon, fluorine, fluorine dimers, chlorine, chlorine dimers, mercury, nitrogen trifluoride, sulfur hexafluoride, a rare gas, a rare earth gas, a transition metal gas, a lanthanide metal gas, a halide containing gas, a mercury halide gas, or some combination thereof.

In some embodiments, the electrodeless lamp includes a plasma generated using a rare earth gas and a mercury gas. In one such embodiment, the light generated by the electrodeless lamp is in a spectral region from about 230 nm to about 480 nm. In another embodiment, the light generated by the electrodeless lamp includes excimer radiation. In one such embodiment, the electrodeless lamp includes about 1 bar or more of background rare gas and about 1 bar or less of a halide containing gas.

In one embodiment, the electrodeless lamp includes a plasma having a geometry shaped to substantially match collection optics of a system configured to inspect the specimen. In another embodiment, the electrodeless lamp includes a bulb configured to optimize a shape of a plasma within the bulb to a collector of a system configured to inspect the specimen. In an additional embodiment, an excitation volume of the electrodeless lamp is substantially matched to a field of view of collection optics of a system configured to inspect the specimen. In a further embodiment, the electrodeless lamp includes a cylindrically shaped plasma substantially matched to image onto the specimen in the system.

In one embodiment, the electrodeless lamp is substantially flat on one side and has a substantially hemispherical shape. In another embodiment, the electrodeless lamp includes a bulb in which a focusing element is disposed such that the electrodeless lamp is configured for substantially high numerical aperture focus. In an additional embodiment, the electrodeless lamp is configured to have an etendue that substantially matches illumination requirements of the system.

In one embodiment, the electrodeless lamp includes a plasma having a diameter of about 100 µm to about 2 mm. In another embodiment, the electrodeless lamp includes a plasma region having a volume of about 0.1 mm to about 2 mm in any direction.

In one embodiment, the electrodeless lamp includes a plasma excited without introducing electrodes or a heat sensitive material near a region of the plasma. In another embodiment, the electrodeless lamp includes a plasma driven by an oscillatory magnetic field. In an additional embodiment, the electrodeless lamp includes a plasma driven by an oscillatory electric field. Each of the embodiments of the system described above may be further configured as described herein.

Another embodiment relates to a system configured to inspect a specimen. The system includes an electrodeless lamp configured to generate light. The system also includes one or more optical elements configured to direct the light to the specimen. In addition, the system includes a detection subsystem configured to generate output responsive to light from the specimen. The output can be used to detect defects on the specimen.

In one embodiment, the system is configured for bright field inspection of the specimen. In another embodiment, the system is configured for dark field inspection of the specimen. In an additional embodiment, the specimen includes a wafer. In a further embodiment, the specimen includes a patterned wafer. In some embodiments, the specimen includes a reticle. Each of the embodiments of the system described above may be further configured as described herein.

An additional embodiment relates to a method for providing illumination of a specimen for inspection. The method includes illuminating the specimen during the inspection with light generated by an electrodeless lamp. The method may include any other step(s) of any other method(s) described herein. Each of the steps of the method may be performed as described herein. In addition, the electrodeless lamp may be configured according to any of the embodiments described herein. Furthermore, the method may be performed by any of the system embodiments described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
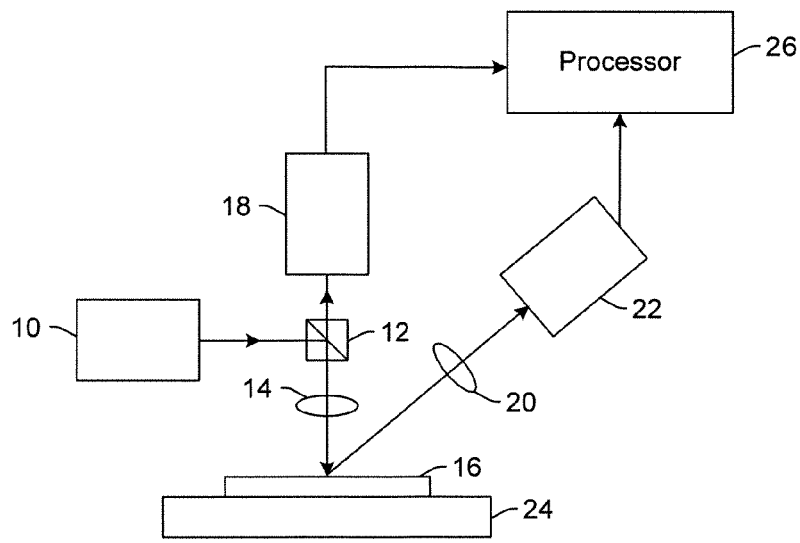
FIG. 1 is a schematic diagram illustrating a side view of one embodiment of a system configured to configured to inspect a specimen.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer, a photomask, or a reticle. However, it is to be understood that the methods and systems described herein may be used for providing illumination for inspection of any other specimen known in the art and/or inspecting any other specimen known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

The terms "reticle" and "photomask" are used interchangeably herein. A reticle generally includes a transparent substrate such as glass, borosilicate glass, and fused silica having opaque regions formed thereon. The opaque regions may be replaced by regions etched into the transparent substrate. Many different types of reticles are known in the art, and the term reticle as used herein is intended to encompass all types of reticles.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a system configured to inspect a specimen. In one embodiment, the system is configured for bright field (BF) inspection of the specimen. In another embodiment, the system is configured for dark field (DF) inspection of the specimen. For example, the system shown in FIG. 1 includes a BF channel and a DF channel. However, the inspection system may include a BF channel or a DF channel. The BF channel and the DF channel are configured to generate inspection output for the specimen. It is noted that FIG. 1 is provided herein to generally illustrate one embodiment of a configuration for the system. Obviously, the system configuration described herein may be altered to optimize the performance of the system as is normally performed when designing a commercial inspection system. In addition, the systems described herein may be implemented using an existing inspection system (e.g., by adding one or more light sources described herein to an existing inspection system or replacing one or more light sources of an existing inspection system with one or more light sources described herein). Alternatively, the system described herein may be designed "from scratch" to provide a completely new system.

The inspection system shown in FIG. 1 includes light source 10 (i.e., an illumination source). Light source 10 may be configured according to any of the embodiments described herein. In particular, light source 10 is an electrodeless lamp configured to generate light. The inspection system may also include two or more light sources (not shown). The two or more light sources may be configured similarly or differently. For example, the light sources may be configured to generate light having different characteristics (e.g., wavelength, polarization, etc.) that can be directed to a specimen at the same or different angles of incidence and at the same or different time. The two or more light sources may be configured according to any of the embodiments described herein. In addition, one of the light sources may be configured according to any of the embodiments described herein, and another light source included in the system may include any other light source known in the art (e.g., a laser).

The system also includes one or more optical elements configured to direct the light to the specimen. For example, the one or more optical elements may include beam splitter 12 and objective 14. Beam splitter 12 is configured to direct light from light source 10 to objective 14. Objective 14 is configured to focus the light from beam splitter 12 onto specimen 16 at a substantially normal angle of incidence. However, the system may be configured to direct the light to the specimen at any suitable angle of incidence. Beam splitter 12 may include any appropriate optical component known in the art. Objective 14 may include any appropriate refractive optical component known in the art. In addition, although objective 14 is shown in FIG. 1 as a single refractive optical component, it is to be understood that objective 14 may include one or more refractive optical components and/or one or more reflective optical components.

In one embodiment, the specimen includes a wafer. In another embodiment, the specimen includes a patterned wafer. In an additional embodiment, the specimen includes a reticle. Therefore, the system may be configured for inspection of a wafer, a patterned wafer, and a reticle. The specimen may be further configured as described herein.

The system also includes a detection subsystem configured to generate output responsive to light from the specimen. The detection subsystem may include multiple, independent detection channels. Each detection channel is configured to collect light scattered or reflected from the specimen under test over a unique set of collection angles. In addition, although embodiments are described further herein as including a BF channel and a DF channel, it is to be understood that the detection subsystem may include any combination of one or more detection channels (e.g., one BF channel and/or one or more DF channels). Moreover, the detection subsystem may include a number of detection channels, and output generated by all of the detection channels or fewer than all of the detection channels may be used by a processor as described further herein. The output generated by a particular combination of detection channels that are used by a processor as described further herein may be selected based on, for example, characteristics of the specimen, characteristics of the defects of interest, and characteristics of the inspection system.

In the embodiment shown in FIG. 1, light reflected from specimen 16 is collected by objective 14 and passes through beam splitter 12 to detector 18. Detector 18 may include any appropriate detector known in the art. Detector 18 is configured to generate inspection output for specimen 16. In addition, detector 18 may include an imaging detector. Therefore, the inspection output generated by detector 18 may include image data. As shown in FIG. 1, objective 14 is configured to collect light specularly reflected from the specimen, and detector 18 is configured to detect light specularly reflected from the specimen. Therefore, objective 14 and detector 18 form the BF channel of the inspection system. As such, the BF channel of the inspection system is configured to generate inspection output for the specimen. In addition, the BF channel of the inspection system may be configured to generate inspection output that includes image data.

Light scattered from specimen 16 is collected by objective 20, which directs the collected light to detector 22. Objective 20 may include any appropriate refractive optical component known in the art. In addition, although objective 20 is shown in FIG. 1 as a single refractive optical component, it is to be understood that objective 20 may include one or more refractive optical components and/or one or more reflective optical components. Objective 20 may be configured to collect light scattered from the specimen at any suitable scattering angles. In addition, the scattering angles at which objective 20 is configured to collect light scattered from the specimen may be determined based on one or more characteristics (e.g., of patterned features (not shown) or defects of interest (not shown)) of the specimen.

Detector 22 may include any appropriate detector known in the art. Detector 22 is configured to generate inspection output for specimen 16. In addition, detector 22 may include an imaging detector. Therefore, the inspection output generated by detector 22 may include image data. As shown in FIG. 1, objective 20 is configured to collect light scattered from the specimen, and detector 22 is configured to detect light scattered from the specimen. Therefore, objective 20 and detector 22 form the DF channel of the inspection system. As such, the DF channel of the inspection system is configured to generate inspection output for the specimen. In addition, the DF channel of the inspection system may be configured to generate inspection output that includes image data.

In some embodiments, the BF channel and the DF channel are configured to generate the inspection output in the deep ultraviolet (DUV) spectrum. For example, as described further herein, light source 10 may be configured to generate light in the DUV spectrum. In addition, detectors 18 and 22 may be configured to detect light reflected and scattered, respectively, in the DUV spectrum. However, the BF and DF channels may also or alternatively be configured to generate the inspection output in any other suitable spectrum (e.g., DUV, ultraviolet (UV), visible, vacuum ultraviolet (VUV), or some combination thereof), which may vary depending on, for example, the spectral region in which light source 10 generates light.

During generation of the output by the BF and DF channels of the inspection system, specimen 16 may be disposed on stage 24. Stage 24 may include any appropriate mechanical and/or robotic assembly known in the art (e.g., a scanning stage configured to support the specimen under test).

The system may also include processor 26. Processor 26 may be coupled to detectors 18 and 22 such that the processor can receive output from detectors 18 and 22. Processor 26 may be coupled to the detectors in any suitable manner known in the art (e.g., via a transmission medium (not shown) that may include "wired" and/or "wireless" portions, via electronic components (not shown) interposed between each of the detectors and the processor, etc.).

The output generated by the detection subsystem (e.g., output generated by detectors 18 and/or 22) can be used to detect defects on specimen 16. For example, processor 26 may be configured to use the output generated by the detection subsystem to detect defects on the specimen. The processor may be configured to detect the defects on the specimen using the output and any appropriate method and/or algorithm known in the art. The processor may also be configured to perform any other step(s) of any other method(s) described herein.

Processor 26 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

The system shown in FIG. 1 may also include any other suitable components (not shown) known in the art. Furthermore, light sources described herein can be used in a commercially available inspection system such as the 2360, 2365, 2371, and 23xx systems that are available from KLA-Tencor, San Jose, Calif. In addition, the electrodeless lamp embodiments described herein may be used in any other appropriate system, some examples of which are illustrated in U.S. Pat. Nos. 5,864,394 to Jordan III et al., 6,313,467 to Shafer et al., 6,633,831 to Nikoonahad et al., 6,862,096 to Vaez-Iravani et al., and 6,879,391 to Danko, which are incorporated by reference as if fully set forth herein.

Furthermore, the system shown in FIG. 1 may be configured and used as a metrology system (e.g., as a system configured to measure one or more characteristics of one or more patterned features formed on the specimen). The metrology system may be configured to perform any measurements known in the art such as optical critical dimension (OCD) measurements.

The embodiments of the system shown in FIG. 1 may be further configured as described herein. In addition, the system may be configured to perform any step(s) of any of the method embodiments described herein. The embodiments of the system shown in FIG. 1 have all of the advantages of other embodiments described herein.

FIG. 1 also illustrates a system configured to provide illumination of a specimen for inspection. The system includes an electrodeless lamp (e.g., light source 10) configured to generate light. The system is further configured such that the light illuminates specimen 16 during inspection. For instance, as described above, the system may include beam splitter 12 and objective 14 that are configured to direct light from light source 10 onto the specimen during inspection such that the light illuminates the specimen during inspection. In addition, the electrodeless lamp may be configured to direct the light onto the specimen during inspection. Furthermore, the system may include any other suitable optical component(s) known in the art configured to direct the light from the electrodeless lamp to the specimen during inspection. This system may be further configured as described herein.

The embodiments described herein are configured to use one or more electrodeless lamps for patterned wafer inspection, other specimen inspection (unpatterned wafer inspection, reticle inspection), or metrology. In particular, one embodiment of a method for providing illumination of a specimen for inspection includes illuminating the specimen during the inspection with light generated by an electrodeless lamp. This method may include any other step(s) of any other method(s) described herein. The steps of the method may be performed as described herein. The electrodeless lamp used in the method may be configured according to any of the embodiments described herein. In addition, the method may be performed by any of the system embodiments described herein. Furthermore, the embodiment of the method described above has all of the advantages of other embodiments described herein.

In one embodiment, the electrodeless lamp has an emissivity of greater than about 0.1. In another embodiment, the light generated by the electrodeless lamp includes DUV light, UV light, visible light, or some combination thereof. In an additional embodiment, the light generated by the electrodeless lamp includes broadband light. In some embodiments, the light generated by the electrodeless lamp includes light in a band from about 180 nm to about 450 nm. In a further embodiment, the light generated by the electrodeless lamp includes light in a spectral region from about 200 nm to about 450 nm. In yet another embodiment, the electrodeless lamp includes a plasma from which collected radiation between about 200 nm and about 450 nm is greater than about 3 W.

The electrodeless lamp includes an electrodeless produced plasma. In particular, in one embodiment, the electrodeless lamp includes a plasma excited without introducing electrodes or a heat sensitive material near a region of the plasma. Electrodeless produced plasmas can be advantageously used to provide relatively high brightness radiation in the DUV region. In addition, electrodeless produced plasmas can be used to provide substantially high brightness radiation in the DUV, UV, and visible regions, or some combination thereof. This broadband spectral brightness has value for flexible, sensitive wafer inspection today and in the near future. The performance of the electrodeless lamps described herein can be optimized for microelectronics inspection applications in a number of ways. For example, optimizing the operation of DUV electrodeless lamps for use as sources in applications for inspection such as semiconductor wafer inspection may include optimizing the pressure, gas type, energy deposition, and energy deposition profile of the lamp while at the same time eliminating the need for electrodes.

The targeted properties of the plasma-based electrodeless light source may include an energy pumped plasma from a gas or gas mixture, emissivity (hence pressure) of at least about 0.1 (although the emissivity may be about 0.05, about 0.1, about 0.2, etc.), partial pressure in a range of about 1 atm to about 40 atm or at least 1 atm, a plasma range limited to a relatively small volume between about 0.1 mm to about 2 mm (e.g., about 0.5 mm) in any direction to conservatively manage input, an etendue that substantially matches an illumination etendue, a managed heat, temperature of the plasma between about 9,000 K and 20,000 K, a plasma excited in a way that does not introduce electrodes or other heat sensitive materials near the plasma region, and an entire light source assembly configured to allow relatively efficient transmission of light in the wavelength band of about 180 nm to about 450 nm and with sufficient etendue to substantially match the illumination requirements of the inspection system. In one embodiment, therefore, the electrodeless lamp is configured to have an etendue that substantially matches illumination requirements of the system. In addition, the shortest wavelength of light emitted by the lamp embodiments described herein may vary depending on the housing of the lamp embodiments. For example, if the lamp housing is formed of a material that is relatively transparent at wavelengths of about 150 nm and above, the lamp may be configured for inspection applications at wavelengths of about 150 nm and above. Therefore, the electrodeless lamps described herein may be used to provide light in the VUV wavelength range in addition to or instead of light in other wavelength ranges described herein.

Briefly, some advantages of using an electrodeless lamp as a relatively high brightness source include: a) elimination of electrodes in the lamp provides a lamp that does not degrade in time; b) the elimination of electrodes allows the lamp to be designed so that substantially all of the excitation energy can be deposited in the region of the lamp in which energy is collected by the system illuminator or lamp optics; c) the geometry of the plasma can be shaped to substantially match that of the collection optics; d) a cylindrical geometry can be generated which, when observed axially, can produce a lamp brightness in excess of that available from a spherically symmetric light source; e) higher brightnesses can be achieved compared to electrode produced plasmas due to 1) the ability to concentrate an excitation source in the region of interest thereby not having to contend with repelling electrons in the excitation region and 2) the ability to achieve substantially higher excitation power densities and hence temperatures; f) ohmic losses in the lamp (e.g., unused ohmic losses in the electrodes of currently used lamps) are substantially eliminated making for a higher efficiency lamp; and g) the elimination of electrodes eliminates a relatively large source of short term and long range degradation and, importantly, variability and noise in lamp output and spectrum.

In one embodiment, the electrodeless lamp includes a plasma generated using a single gas. In a different embodiment, the electrodeless lamp includes a plasma generated using a combination of gases. In another embodiment, the electrodeless lamp is filled with a gas that includes argon (Ar), krypton (Kr), xenon (Xe), fluorine (F), F dimers, chlorine (Cl), Cl dimers, mercury (Hg), nitrogen trifluoride ($NF_3$), sulfur hexafluoride ($SF_6$), a rare gas, a rare earth gas, a transition metal gas, a lanthanide metal gas, a halide containing gas, a Hg halide gas, or some combination thereof.

In one example, nontraditional fill gases may be used in an electrodeless lamp for DUV inspection applications in which the wavelengths of interest are roughly in the spectral region from about 200 nm to about 450 nm. In addition to commonly used gases such as Ar, Kr, Xe, and Hg, gases such as Cl dimers, F dimers, rare earths, transition metals, and lanthanide metals are capable of providing substantially favorable working media in this wavelength range. These materials may be introduced to the lamp in the form of molecular species with relatively high vapor pressures. Example of appropriate gases also include, but are not limited to, Hg halides, $NF_3$, $SF_6$, diatomic halogens such as diatomic chlorine ($Cl_2$), and a host of other combination gases. These gases will only be present as atomic constituents within the relatively high temperature plasmas, and their emission can be optimized in the wavelength range of about 200 nm to about 450 nm, for example, by varying the plasma temperature. Feed material (fill materials at room temperature), which are atomic already or which are diatomic gases of a single atomic species, furthermore will not be consumed in the apparatus.

In one embodiment, the light generated by the electrodeless lamp includes excimer radiation. In one such embodiment, the electrodeless lamp includes about 1 bar or more of background rare gas and about 1 bar or less of a halide containing gas. For example, gas mixtures of Ar and F, in the case of relatively high background pressure or partial pressure (1 bar roughly or more) of Ar, will advantageously give rise to excimer emission (emission of F on a background of Ar) in a relatively copious quantity. In addition, unlike excimer laser light sources, the excimer emission of the lamp embodiments described herein is incoherent emission. Furthermore, unlike excimer laser light sources that produce narrowband light, the lamp embodiments described herein produce broadband light. Therefore, mixtures of Ar or Kr, for example, with diatomic halide species are particularly attractive feed materials.

Ideal gases for uses in embodiments described herein may have a relatively high 1 μm absorption in the plasma state, relatively high emissivity at wavelengths from about 250 nm to about 400 nm, relatively low emissivity outside of wavelengths from about 250 nm to about 400 nm, ignite relatively easily, and do not substantially attack the glass or other materials of the lamps and do not leak out of the glass or other materials of the lamp.

The plasma temperature in the region of highest brightness can be readily controlled and held substantially constant using excitation source pumped plasmas. It may also be desirable to optimize the brightness of the lamp and the average power of the lamp without exceeding a blackbody temperature that would produce substantial amounts of "out of band" DUV radiation above the bandgap for absorption of common UV transparent materials such as fused silica, magnesium fluoride ($MgF_2$), and similar materials. For example, while temperatures as high as about 50,000 K can be achieved in discharges (e.g., radio frequency (RF) excited discharges and light produced discharges at relatively high pump powers and tight focus), it is important to recognize that above about 20,000 K the amount of blackbody radiation produced above the bandgap of the containing envelope of the lamp, be it fused silica, $MgF_2$, lithium fluoride (LiF), or other UV transparent materials is sufficiently high that the envelope will absorb the radiation and fracture or melt. Nearly three orders of magnitude more radiation within absorbing regions of fused silica is produced in a temperature range of about 25,000 K to about 50,000 K than the 10,000 K plasma range. Accordingly, exciting the plasma to temperatures between about 10,000 K and about 20,000 K is easily achieved and maintained in a properly designed electrodeless pumped plasma.

Configuring the focus of the excitation source or excitation sources used to sustain the plasma action appropriately is advantageous. In particular, inspection systems most efficiently collect and deliver light to the specimen plane using certain plasma shapes and sizes. For BF inspection systems used beyond the year 2005, shrinking pixel sizes and increased imaging computer inspection speeds will demand that plasmas roughly 1 mm in dimension are provided. In one embodiment, the electrodeless lamp includes a cylindrically shaped plasma substantially matched to image onto the specimen in the specimen. For example, "hockey puck" geometries in which the thickness of the puck is substantially matched to the depth of focus in the system and the puck diameter is roughly about 1 mm or a couple of hundred of μm are preferred. Therefore, relatively high numerical aperture (NA) short focal length delivery from one or more excitation sources are expected to best approach this geometry.

Light generated by a plasma that has a generally ellipsoidal shape may be directed to one or more reflectors or other optical components of the inspection system that direct only some cylindrical section of the light generated by the plasma to the specimen. This cylindrical section of the light may be directed or reflected in some nearly parallel way to a mirror, condenser, homogenizer, or some combination thereof. The illumination optics used in the system for the lamp embodiments described herein may be selected such that about $\pi$ sr from an about $4\pi$ sr plasma is directed to the specimen. In this manner, the entire cross-section of light generated by the plasma may not be directed to the specimen.

In another embodiment, an excitation volume of the electrodeless lamp is substantially matched to a field of view of collection optics of a system configured to inspect the specimen. In one embodiment, the electrodeless lamp includes a plasma region having a volume of about 0.1 mm to about 2 mm in any direction. In an additional embodiment, the electrodeless lamp includes a plasma having a geometry shaped to substantially match collection optics of a system configured to inspect the specimen. In this manner, the plasma excitation may be shaped such that the excitation volume of the plasma is substantially matched to the collection optics field of view appropriate for inspection such as wafer and/or reticle inspection.

The field of view on the wafer may have a shape such as a rectangular, square, or circular shape. In addition, the field of view on the wafer may be about 1000 pixels to about 8000 pixels wide. The size of the pixels may be about 50 nm to about 300 nm depending on the inspection application and inspection system configuration. The NA may be up to about 0.9. In addition, higher brightness is desirable as the etendue decreases.

In some embodiments, the light from the lamp may not be directed to the specimen across all of the solid angles encompassed by the NA. Instead, the light from the lamp may be directed to the specimen across a "ring" within the NA that subtends a solid angle of about 10 degrees to about 15 degrees, which may vary depending on the NA of the illumination subsystem of the inspection system.

In one embodiment, a system described herein includes one or more electrodeless lamps at pressures above about 0.5 atm (at their working temperatures) that are configured to produce light for inspection (e.g., wafer inspection). In some embodiments, the lamp(s) produce light in the region of wavelengths between about 200 nm and about 400 nm. For example, in one embodiment, the electrodeless lamp is at a pressure of above about 1 atm at a working temperature of the electrodeless lamp, and the light generated by the electrodeless lamp includes light in a spectral region from about 200 nm to about 400 nm.

In another embodiment, the light generated by the electrodeless lamp has a spectral brightness exceeding about 2 $W/mm^2$-sr in an integral region of an electromagnetic spectrum from about 200 nm to about 400 nm. In this manner, the system may include one or more electrodeless lamps as light source(s), and the one or more electrodeless lamps may have spectral brightness exceeding about 2 $W/mm^2$-sr in the integral region of the electromagnetic spectrum from about 200 nm to about 400 nm. In addition, the one or more electrodeless lamps may have spectral brightness of about 10 $W/mm^2$-sr to about 40 $W/mm^2$-sr. In a further embodiment, the electrodeless lamp(s) are configured to generate in excess of about 3 W of average power within any band contained within the region between about 200 nm and about 450 nm. In this manner, in some embodiments, light generated by the electrodeless lamp has an average power in excess of about 3 W within any band in a region between about 200 nm and about 450 nm. Therefore, the electrodeless lamps described herein may be configured to generate broadband light that can be used for broadband inspection of a specimen. In addition, the electrodeless lamps are configured to generate incoherent light.

In one embodiment, the electrodeless lamp includes a plasma driven by an oscillatory magnetic field. In another embodiment, the electrodeless lamp includes a plasma driven by an oscillatory electric field. In this manner, the excitation source may include an electromagnetic excitation source. For example, the electromagnetic excitation source may be an RF source that can generate about a 1 GHz to many GHz electric field. In another example, the electromagnetic excitation source may be a microwave cavity that is configured to generate electric and magnetic fields. The electromagnetic excitation source may function as a relatively high power amplifier that is focused to a relatively small region proximate the plasma. In a different embodiment, the excitation source includes an electron source. For example, the electron source may be an electron gun. Electrodeless lamps that include plasmas driven by an oscillatory magnetic or electric field may be further configured as described herein.

In some embodiments, the system includes an excitation source for the excitation of the plasma(s) in the electrodeless lamp(s) in cylindrical geometries such that the plasma axis length does not produce an average plasma opacity over this region of greater than one e-folding from "end-cap" to "end-cap." In this manner, the electrodeless lamp may include a plasma having a plasma axis length, and the plasma does not produce an average plasma opacity over the plasma axis length of greater than about 1 e-folding from one end cap to another end cap of the electrodeless lamp.

In another embodiment, the system is configured to use excitation from one or more excitation sources to form disc or hockey puck shaped plasmas that are relatively well matched to image onto the wafer plane in inspection systems. In a further embodiment, the electrodeless lamp includes a plasma having a diameter of between about 100 μm and about 2 mm. In an additional embodiment, the system is configured to use one or more excitation sources to ignite a plasma in the electrodeless lamp, and the power of the excitation source(s) is in excess of about 100 W In some embodiments, the system is configured to use one or more "igniter" electrodes in conjunction with the over all electrodeless produced plasma. These one or more electrodes may be used to reduce the intensity of the excitation source that initiates the plasma. In a further embodiment, the electrodeless lamp includes an electrodeless produced plasma in which the collected radiation between about 200 nm and about 450 nm is more than about 3 watts.

In an additional embodiment, one or more materials are introduced to the lamp(s). The one or more materials may include fill gases such as Ar, Kr, Xe, F, Cl, $NF_3$, $SF_6$, any other rare gas or halide containing gas, or some combination thereof. In another embodiment, the electrodeless produced plasma is configured to produce excimer radiation by using about 1 bar or more of background rare gas along with a similar or lower fill pressure (i.e., the initial or cold pressure) of halide containing gas. In one embodiment, the electrodeless lamp has a partial pressure in a range of about 1 atm to about 40 atm. In another embodiment, a fill pressure of gases in the electrodeless lamp is about 4 atm or higher. In some embodiments, the lamp is configured for fill pressures of gases to as much as about 10 atm or about 10 bar. In another embodiment, the lamp is configured for fill pressures of gases to as much as about 4 atm to about 10 atm or bar or higher. Higher fill pressures may be advantageous to increase the excitation of the plasma, which may increase the average power that can be achieved by the plasma. In other words, using higher fill pressures may advantageously increase the ratio of absorbed power to radiated power of the plasma. In one embodiment, the electrodeless lamp includes a plasma generated using a rare earth gas and a Hg gas. In one such embodiment, the light generated by the electrodeless lamp is in a spectral region from about 230 nm to about 480 nm. The electrodeless lamp may include an electrodeless produced plasma that includes a combination of rare earth (e.g., Xe, Ar, etc.) and Hg gases to optimize spectral brightness in the wavelength region of about 230 nm to about 480 nm. For example, the electrodeless produced plasma may include about 1 atm fill of Ar, about 4 atm or higher fill of Ar, about 1 atm fill of Xe, about 4 atm or higher fill of Xe, a combination of Hg and Xe, and about 1 atm fill of Xe with $Cl_2$.

In some embodiments, a fill gas in the electrodeless lamp has an opacity at a working temperature and pressure of the electrodeless lamp that does not exceed about 10% reabsorption of about 200 nm to about 450 nm radiation emitted from a center of the electrodeless lamp. In this manner, the opacity of fill gases used in the electrodeless lamp at the working temperature and pressure of the lamp does not exceed about 10% reabsorption of about 200 nm to about 450 nm radiation emitted from the center of the lamp.

In another embodiment, a temperature of the plasma in the electrodeless lamp is between about 10,000 K and about 30,000 K for any of the fill gases described herein. In one embodiment, therefore, the electrodeless lamp includes a plasma at a temperature of about 10,000 K to about 30,000 K. However, in a different embodiment, the electrodeless lamp includes a plasma at a temperature of about 9,000 K to about 20,000 K.

In one embodiment, the electrodeless lamp is substantially flat on one side and has a substantially hemispherical shape. For example, the electrodeless lamp may be substantially flat on one side (e.g., such that the lamp has a shape approximately similar to a hemisphere) to reduce the distance between the entrance of the excitation source to the working medium to its focal point. This concept and related bulb design concepts may be employed to optimize the shape of the plasma to the collector of the inspection system. In one embodiment, therefore, the electrodeless lamp includes a bulb configured to optimize a shape of a plasma within the bulb to a collector of a system configured to inspect the specimen.

In one embodiment, the electrodeless lamp includes a bulb in which a focusing element is disposed such that the electrodeless lamp is further configured for substantially high NA focus. For example, in some embodiments, the electrodeless lamp includes a bulb with an internal lens or curved reflector to achieve relatively high NA focus. In addition, the plasma source may be positioned at approximately the center of a spherical reflector that will redirect some light generated by the plasma back into the plasma thereby causing further heating of the plasma. While the plasma may be relatively optically thin (and not substantially absorptive), if the Q of the cavity is relatively high (e.g., not much loss in the reflector or in the quartz bulb) then there are chances for photons to be absorbed in the plasma. For example, the plasma will radiate over almost $4\pi$ sr, but about $\pi$ sr of the light may be collected. Therefore, the uncollected light may be used to reheat the plasma and drive up the temperature and brightness. The spherical reflector may have holes formed therethrough to allow for the collection of the light, but these holes may not reduce the Q much for photons that are bouncing back and forth across the spherical reflector away from the collection optics until they get absorbed by the plasma. To optimize this effect, the absorption at the reflector (1-R) may be small compared to the absorption at the plasma. As such, the reflector may have a substantially high R at the wavelengths at which the plasma radiates. The bulb wall absorption losses are also preferably relatively low for this to work well as high absorption at the bulb wall would reduce the overall cavity Q. This effect may combat the effect of the plasma burning away from the focal point of the excitation source. Pumping with reflected light over a substantially large NA would tend to counteract this effect.

There are additional ways to excite a relatively high pressure, spatially limited plasma. For example, an RF electrical amplifier may be configured to drive a tuned inductor (e.g., a Helmholtz coil) or capacitor to create substantially large oscillatory magnetic and electric fields, respectively. A critical field strength will cause ionization and the resulting oscillatory electrons will drive plasma temperature in the same way that electrons drive discharge arc or inductive loop based plasma sources.

Figure 2:
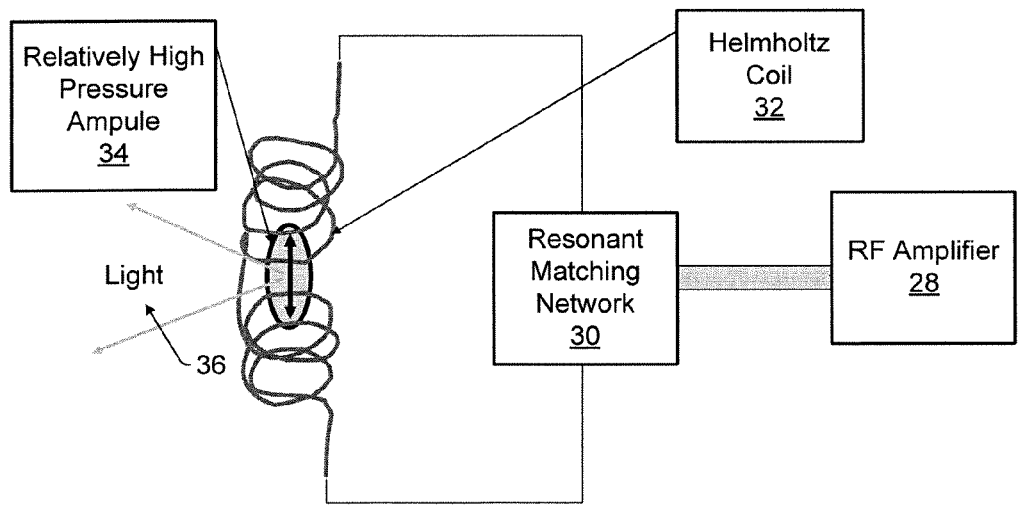
FIGS. 2 and 3 are schematic diagrams illustrating a side view of various embodiments an electrodeless lamp.
Figure 3:
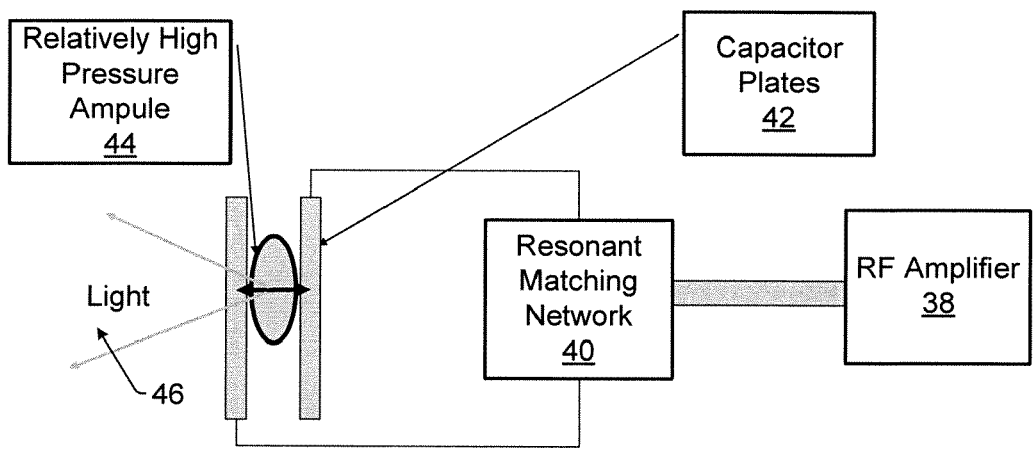

FIGS. 2 and 3 illustrate various embodiments of an electrodeless lamp. In particular, FIG. 2 illustrates one method for delivering excitation power to a contained relatively small, relatively high pressure plasma. In this embodiment, a relatively high power amplifier is used to create focus to a relatively small region. As shown in FIG. 2, this embodiment of an electrodeless lamp includes RF amplifier 28 coupled to resonant matching network 30. The RF amplifier and the resonant matching network may include any suitable components known in the art. The resonant matching network may be configured to operate at about 50 ohms. The resonant matching network is coupled to Helmholtz coil 32 to create a relatively high strength oscillatory magnetic field. The Helmholtz coil may include any suitable Helmholtz coil known in the art.

Relatively high pressure ampule 34 (having dimensions of about 1 mm by about 2 mm and having a roughly ellipsoidal shape) contains the plasma gas mixture. The ampule may have any other suitable configuration. The plasma gas mixture may include any of the gas mixtures described herein. As further shown in FIG. 2, light 36 is output from the ampule, which may include DUV light, UV light, visible light, or some combination thereof. The embodiment of the electrodeless lamp shown in FIG. 2 may be further configured as described herein. The embodiment of the electrodeless lamp shown in FIG. 2 may be included in any of the systems described herein. In addition, the embodiment of the electrodeless lamp shown in FIG. 2 has all of the advantages of other embodiments described herein.

FIG. 3 illustrates another method for delivering excitation power to a contained relatively small, relatively high pressure plasma. As shown in FIG. 3, this embodiment of an electrodeless lamp includes RF amplifier 38 coupled to resonant matching network 40. The RF amplifier and the resonant matching network may include any suitable components known in the art. The resonant matching network may be configured to operate at approximately 50 ohms. The resonant matching network is coupled to capacitor plates 42 that are configured to create a relatively high strength oscillatory electric field. In this manner, electromagnetic sources may be used to drive RF to a many GHz resonant electric field. In a similar manner (not shown), electromagnetic sources may be used to drive microwave cavities with electric and magnetic fields. The capacitor plates may have any suitable configuration known in the art.

Relatively high pressure ampule 44 (having dimensions of about 1 mm by about 2 mm and having a roughly ellipsoidal shape) contains the plasma gas mixture. The ampule may have any other suitable configuration. The plasma gas mixture may include any of the gas mixtures described herein. As further shown in FIG. 3, light 46 is output from the ampule, which may include DUV light, UV light, visible light, or some combination thereof. The embodiment of the electrodeless lamp shown in FIG. 3 may be further configured as described herein. The embodiment of the electrodeless lamp shown in FIG. 3 may be included in any of the systems described herein. In addition, the embodiment of the electrodeless lamp shown in FIG. 3 has all of the advantages of other embodiments described herein.

The configuration of the electrodeless lamps described herein may be further selected based on Babucke et al., J. Phys. D, App. Phys. 24 1316 (1991), Derra et al., J. Phys. D, App. Phys., 38 2995, A. T. M. Wilburs and D. C. Schram, J. Quant. Spec. and Radiat. Transfer, 46 299-308 (1991), and D. Erskine et al., J. Quant. Spec. and Radiat. Transfer, 51(12), 97-100 (1994), which are incorporated by reference as if fully set forth herein.

Further modifications and alternative embodiments of various aspects of the invention may be apparent to those skilled in the art in view of this description. For example, methods and systems for providing illumination of a specimen for inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to provide illumination of a specimen for inspection, comprising an electrodeless lamp configured to generate light, wherein the system is further configured such that the light illuminates the specimen during the inspection, wherein the electrodeless lamp comprises a bulb configured to optimize a shape of a plasma within the bulb to a collector of a system configured to inspect the specimen, and wherein the electrodeless lamp is substantially flat on one side and has a substantially hemispherical shape.

2. The system of claim 1, wherein the electrodeless lamp has an emissivity of greater than about 0.1.

3. The system of claim 1, wherein the light generated by the electrodeless lamp comprises deep ultraviolet light, ultraviolet light, visible light, or some combination thereof.

4. The system of claim 1, wherein the light generated by the electrodeless lamp comprises broadband light.

5. The system of claim 1, wherein the light generated by the electrodeless lamp comprises light in a band from about 180 nm to about 450 nm.

6. The system of claim 1, wherein the light generated by the electrodeless lamp comprises light in a spectral region from about 200 nm to about 450 nm.

7. The system of claim 1, wherein radiation collected from the plasma between about 200 nm and about 450 nm is greater than about 3 W.

8. The system of claim 1, wherein the electrodeless lamp has a partial pressure in a range of about 1 atm to about 40 atm.

9. The system of claim 1, wherein a fill pressure of gases in the electrodeless lamp is about 4 atm or higher.

10. The system of claim 1, wherein the plasma is at a temperature of about 10,000 K to about 30,000 K.

11. The system of claim 1, wherein the plasma is at a temperature of about 9,000 K to about 20,000 K.

12. The system of claim 1, wherein the electrodeless lamp is at a pressure of above about 1 atm at a working temperature of the electrodeless lamp, and wherein the light generated by the electrodeless lamp comprises light in a spectral region from about 200 nm to about 400 nm.

13. The system of claim 1, wherein the light generated by the electrodeless lamp has a spectral brightness exceeding about 2 W/mm$^2$-sr in an integral region of an electromagnetic spectrum from about 200 nm to about 400 nm.

14. The system of claim 1, wherein the light generated by the electrodeless lamp has an average power in excess of about 3 W within any band in a region between about 200 nm and about 450 nm.

15. The system of claim 1, wherein the plasma has a plasma axis length, and wherein the plasma does not produce an average plasma opacity over the plasma axis length of greater than about 1 e-folding from one end cap to another end cap of the electrodeless lamp.

16. The system of claim 1, wherein the plasma is generated using a single gas.

17. The system of claim 1, wherein the plasma is generated using a combination of gases.

18. The system of claim 1, wherein the electrodeless lamp is filled with a gas comprising argon, krypton, xenon, fluoride, fluorine dimers, chlorine, chlorine dimers, mercury, nitrogen trifluoride, sulfur hexafluoride, a rare gas, a rare earth gas, a transition metal gas, a lanthanide metal gas, a halide containing gas, a mercury halide gas, or some combination thereof.

19. The system of claim 1, wherein the plasma is generated using a rare earth gas and a mercury gas, and wherein the light generated by the electrodeless lamp is in a spectral region from about 230 nm to about 480 nm.

20. The system of claim 1, wherein the light generated by the electrodeless lamp comprises excimer radiation, and wherein the electrodeless lamp comprises about 1 bar or more of background rare gas and about 1 bar or less of a halide containing gas.

21. The system of claim 1, wherein the plasma has a geometry shaped to substantially match collection optics of the system configured to inspect the specimen.

22. The system of claim 1, wherein an excitation volume of the electrodeless lamp is substantially matched to a field of view of collection optics of the system configured to inspect the specimen.

23. The system of claim 1, wherein the plasma comprises a cylindrically shaped plasma substantially matched to image onto the specimen in the system.

24. The system of claim 1, wherein a focusing element is disposed in the bulb such that the electrodeless lamp is further configured for substantially high numerical aperture focus.

25. The system of claim 1, wherein the electrodeless lamp is further configured to have an etendue that substantially matches illumination requirements of the system.

26. The system of claim 1, wherein the plasma has a diameter of about 100 μm to about 2 mm.

27. The system of claim 1, wherein the plasma is excited without introducing electrodes or a heat sensitive material near a region of the plasma.

28. The system of claim 1, wherein the plasma is driven by an oscillatory magnetic field.

29. The system of claim 1, wherein the plasma is driven by an oscillatory electric field.

30. The system of claim 1, wherein a fill gas in the electrodeless lamp has an opacity at a working temperature and pressure of the electrodeless lamp that does not exceed about 10% reabsorption of about 200 nm to about 450 nm radiation emitted from a center of the electrodeless lamp.

31. A system configured to inspect a specimen, comprising:
    an electrodeless lamp configured to generate light;
    one or more optical elements configured to direct the light to the specimen;
    a collector configured to collect light from the specimen, wherein the electrodeless lamp comprises a bulb configured to optimize a shape of a plasma within the bulb to the collector, wherein the electrodeless lamp is substantially flat on one side and has a substantially hemispherical shape; and
    a detection subsystem configured to generate output responsive to the light from the specimen, wherein the output can be used to detect defects on the specimen.

32. The system of claim 31, wherein the system is further configured for bright field inspection of the specimen.

33. The system of claim 31, wherein the system is further configured for dark field inspection of the specimen.

34. The system of claim 31, wherein the specimen comprises a wafer.

35. The system of claim 31, wherein the specimen comprises a patterned wafer.

36. The system of claim 31, wherein the specimen comprises a reticle.

37. A method for providing illumination of a specimen for inspection, comprising illuminating the specimen during the inspection with light generated by an electrodeless lamp, wherein the electrodeless lamp comprises a bulb configured to optimize a shape of a plasma within the bulb to a collector of a system configured to inspect the specimen, and wherein the electrodeless lamp is substantially flat on one side and has a substantially hemispherical shape.

* * * * *